United States Patent [19]

Miyagi et al.

[11] 4,112,297
[45] Sep. 5, 1978

[54] INTERFACE FOR USE IN A COMBINED LIQUID CHROMATOGRAPHY - MASS SPECTROMETRY SYSTEM

[75] Inventors: Hiroyuki Miyagi; Fumito Nakajima; Yoshijiro Arikawa, all of Ibaraki, Japan

[73] Assignee: Hitachi, Ltd., Japan

[21] Appl. No.: 811,720

[22] Filed: Jun. 30, 1977

[30] Foreign Application Priority Data

Jun. 30, 1976 [JP] Japan .................................. 51-76362

[51] Int. Cl.$^2$ .......................................... B01D 59/44
[52] U.S. Cl. .................................. 250/288; 250/281; 250/423 R
[58] Field of Search..................250/281, 288, 423 R, 250/425

[56] References Cited

U.S. PATENT DOCUMENTS 4,008,388  2/1977  McLafferty et al. ................ 250/281

*Primary Examiner*—Harold A. Dixon
*Attorney, Agent, or Firm*—Craig & Antonelli

[57] ABSTRACT

A new interface is interposed between a liquid chromatograph and a mass spectrometer, and it consists of a nebulizer, an evaporator and a cooler. An effluent from the liquid chromatograph is nebulized by the nebulizer. The nebulized effluent is heated by the evaporator, and has only its solvent evaporated. A mixed fluid which consists of the evaporated solvent and the nebulized sample is guided to the cooler, and is cooled therein. At this time, the evaporated solvent is condensed again and is separated from the nebulized sample as a liquid. The nebulized sample left behind is guided to an ion source of the mass spectrometer.

7 Claims, 4 Drawing Figures

INTERFACE FOR USE IN A COMBINED LIQUID CHROMATOGRAPHY - MASS SPECTROMETRY SYSTEM

BACKGROUND OF THE INVENTION

This invention relates to an interface for use in a combined liquid chromatography — mass spectrometry system.

A chromatograph is means effective for separating and analyzing a sample, while a mass spectrometer is means effective for obtaining information on the molecular weight and molecular structure of the sample. There has been developed a system in which the chromatograph and the mass spectrometer are coupled and which performs the analyses of a sample continuously from the quantitative analysis to the qualitative analysis. Among such systems, one employing a liquid chromatograph as the chromatograph has the feature of being effective for the continuous analyses of, particularly, a substance which is difficult to be separated and analyzed by the gas chromatography, for example, a substance which is thermally unstable or a substance whose volatility is low. In such combined liquid chromatography — mass spectrometery system, it is necessary to selectively take only the sample out of an effluent from the liquid chromatograph and to supply it to the mass spectrometer. The effluent from the liquid chromatograph contains the sample and a solvent in large quantities relative to the sample, and the solvent must be separated and removed from the effluent. Further, in order to obtain a more accurate mass spectrum of the sample, an enriched sample need be introduced into the mass spectrometer. To this end, an interface is usually provided between the liquid chromatograph and the mass spectrometer. Thus, the two requirements are fulfilled.

As to such interface, there has been known, for example, W. H. McFadden and H. L. Schwartz, "Direct Analysis of Liquid Chromatographic Effluents," Journal of Chromatography, 122 (1976) 389–396, in which a ribbon transport LC - MS interface is disclosed. In this interface, an annular ribbon made of stainless steel circulates through two vacuum locks and a heater which are interposed between the liquid chromatograph and the mass spectrometer. The effluent from the liquid chromatograph is placed on the stainless-steel ribbon. A part of the solvent is removed by heating etc., whereupon the remaining solvent is removed in the two vacuum locks. Lastly, the sample left behind is heated and vaporized by the heater. The vaporized sample is guided to an ion source of the mass spectrometer. Partition plates forming the vacuum locks are provided with slots of very small diameter for passage of the stainless-steel ribbon.

Such interface, however, has the following disadvantages. A preceding sample adhering to the surface of the slot mixes into a succeeding sample, and becomes the cause for the memory effect of the sample spectrum. It is possible that the quality of a sample will be changed by the stainless steel. Further, the change of the quality of the sample is brought about by heating the sample for the vaporization at a high temperature. At a higher solvent flow-rate, sample is lost due to spray evaporation at the first vacuum lock.

SUMMARY OF THE INVENTION

An object of this invention is to provide an interface suitable for a combined liquid chromatography - mass spectrometry system, which is capable of extracting the sample from the effluent of a liquid chromatograph and supplying it for a mass spectrometer without any chemical change in quality thereof.

The object mentioned above is achieved by an interface for use in a combined liquid chromatography - mass spectrometry system which extracts a sample component out of the effluent including the sample component and a solvent component from a liquid chromatograph and supplies the extracted sample component for a mass spectrometer, characterized in that the interface comprises first means for nebulizing the effluent from the liquid chromatograph and heating it in a manner that only the solvent component is evaporated, and second means for separating said nebulized effluent into the nebulized sample component and the evaporated solvent component to extract and supply only the nebulized sample component for the mass spectrometer.

DETAILED DESCRIPTION OF THE PREFERRED EMBODIMENTS

Figure 1:
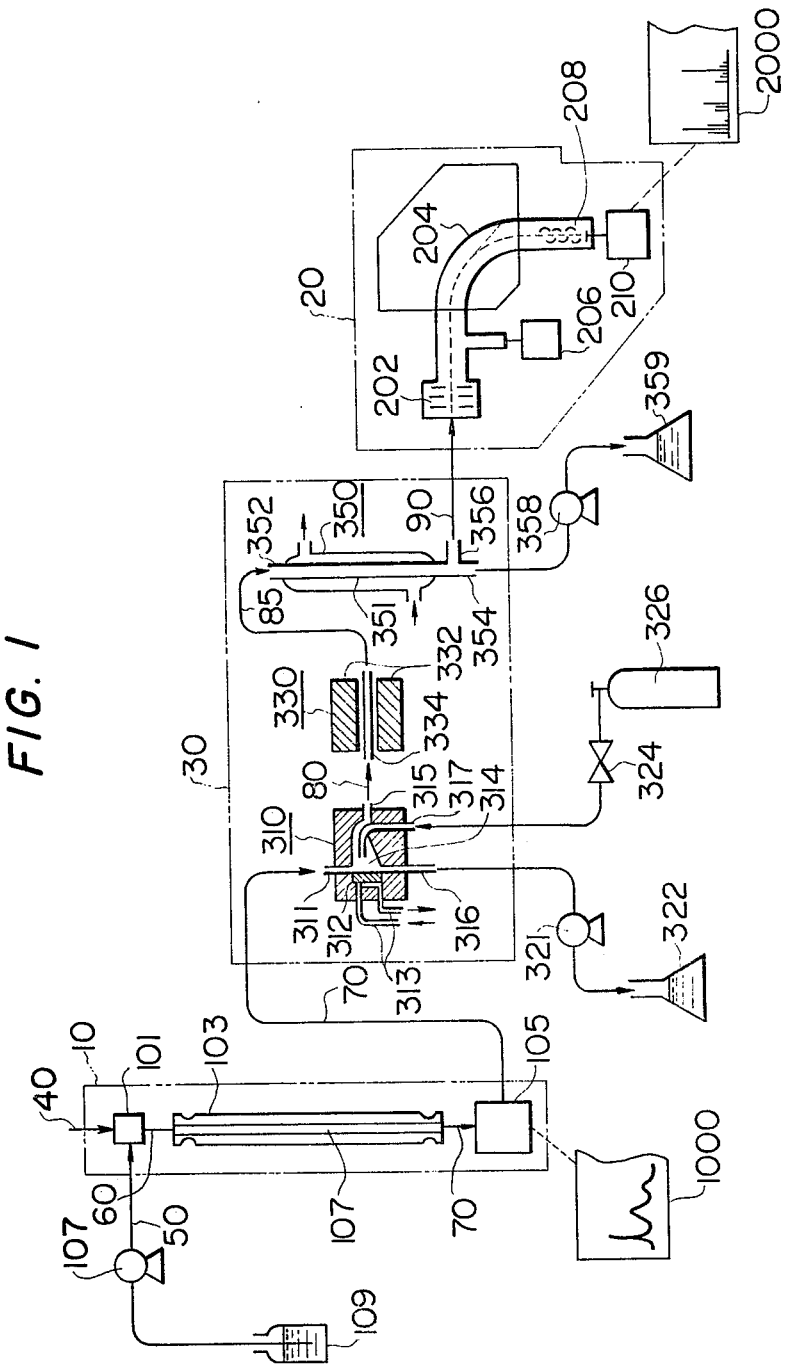
FIG. 1 shows a schematic diagram of a combined liquid chromatography - mass spectrometry system which has an interface according to this invention.

Depicted in FIG. 1 is a combined liquid chromatography mass spectrometry system which has an interface according to this invention. The system is constructed of a liquid chromatograph (hereinafter, abbreviated to "LC") 10, a mass spectrometer (hereinafter, abbreviated to "MS") 20, and an interface 30 interposed therebetween. As is already known, the LC 10 is made up of a sample injector 101, a separation column 103 and a detector 105. The sample injector 101 is connected through a pump 107 to a vessel 109 containing a solvent therein. Used as the solvent is, for example, water, methanol, ethanol, acetone or a mixture thereof. The solvent is pressurized by the pump, and is steadily supplied to the sample injector 101. The separation column 103 is filled with a column packing 107. As the detector 105, there is used a spectrophotometer such as ultraviolet absorption detector, a differential refractometer, or the like.

The interface 30 is made up of a nebulizer 310, an evaporator 330 and a cold trap 350. As the nebulizer 310, one of the ultrasonic type is used in the present embodiment though one of the jet type is also usable. The nebulizer 310 has an effluent inlet 311, an ultrasonic transducer 312, cooling piping 313, a nebulization chamber 314, an outlet 315, a drain 316 and a carrier gas inlet 317. The effluent inlet 311 is connected to the detector 105 of the LC 10, and an effluent from the LC 10 is guided into the nebulizer 310 through the effluent inlet 311. In the present embodiment, an oscillator of lead titanatezirconate (Devilbis 35B) is employed as the ultrasonic transducer 312. The oscillator can generate ultrasonic waves of a frequency of 1.35 MHz at the maximum output of 100 W. As indicated by arrows in the figure, water is caused to flow through the cooling pipe which is disposed at the back of the ultrasonic transducer 312. The ultrasonic transducer 312 can nebulize 5 – 10% of the effluent from the LC 10 as flows in at a flow rate of approximately 1 cc/min. The drain 316 is connected through a pump 321 to a drain pot 322, and the effluent which has not been nebulized in the nebulizer 310 is collected into the drain pot 322 by the action of the pump 321. The carrier gas inlet 317 is connected through a valve 324 to a carrier gas tube 326. A carrier gas in the tube 326 is supplied to the nebulization chamber 314 in order to send out the nebulized effluent within the nebulization chamber 314. The carrier gas does not lower the nebulization efficiency of the ultrasonic transducer 312. As such carrier gas, nitrogen ($N_2$) or an inert gas such as helium (He) and argon (Ar) is used. The evaporator 330 has a heater 332 and an inner tube 334. The tube 334 is connected to the mist outlet 315 of the nebulizer 310. The temperature of the heater 332 must be set at a value of the extent that only the solvent in the nebulized effluent from the nebulizer 310, i.e., only water (boiling point: 100° C), methanol (64.7° C), ethanol (78.3° C), acetone (56.3° C) or a mixture thereof will be evaporated and that a sample will not change in quality. In the present embodiment, this temperature is set at 100° C being the boiling point of water which exhibits the highest boiling point among the solvent components. In general, the sample of a substance to be analyzed by the liquid chromatography, for example, a high-molecular organic compound has not the quality changed by such temperature. The cold trap 350 functioning as a cooler has an upper inlet 352 which is connected to the inner tube 334 of the evaporator 330, lower outlets 354 and 356 in the form of two branches, and a condenser tube 351. The cold trap 350 is supplied with cooling water, which is indicated by arrows in the figure. One lower outlet 354 of the cold trap 350 is connected through a pump 358 to a drain pot 359, while the other outlet 356 is connected to the MS 20. A mixed fluid from the evaporator 330 as consists of the carrier gas, the evaporated solvent and the nebulized sample is cooled by passing through the cold trap 350. At this time, the evaporated solvent is condensed on the inside wall surface of the condenser tube 351 of the cold trap 350 and is discharged to the drain pot 359 by the action of the pump 358. The cold trap 350 can be replaced with a cooler which is made of a Peltier element.

As the MS 20, one of the differential pumping system already known is used, but the invention is not restricted thereto. The nebulized sample and the carrier gas from the interface 30 are conducted to an ion source 202. The ion source 202 will be described in detail later. The carrier gas is discharged to the exterior in the ion source 202, while the sample is ionized and is conducted to and analyzed in an analyzer tube 204. However, in case of employing an MS of any other system than the differential pumping system, the fluid to be supplied thereto must have the carrier gas further removed by an evacuation pump or the like. Reference numerals 206, 208 and 210 designate a total ion monitor, a collector and an amplifier, respectively.

The operation of the above system will now be explained.

The sample 40 to be analyzed is steadily supplied to the sample injector 101, in which it is dissolved into the solvent 50 being pressurized and steadily supplied by the pump 107. A mixed solution 60 consisting of the solvent and the sample is guided to the separation column 103, and has the components analyzed therein. That is, owing to differences in the affinities between the column packing 107 in the separation column 103 and various components of the sample, the sample in the mixed solution 60 is separated. The respective separated components are discharged as the effluent 70 together with the solvent. The effluent 70 exhibits different components versus time. The effluent has the quantities of the components analyzed by the detector 105, with the result that a chromatogram 1000 of the sample is obtained. The effluent 70 contains the solvent the amount of which is very large relative to those of the separated components of the sample.

The effluent 70 from the LC 10 is introduced into the nebulizer 310 through the effluent inlet 311. The effluent 70 passes on the surface of the ultrasonic transducer 312. At this time, it receives ultrasonic energy to become fine mist, which enters the nebulization chamber 314. The effluent nebulized by the nebulizer 310 is conducted to the evaporator 330 by the carrier gas from the carrier gas tube 326. The mixed fluid 80 from the nebulizer 310 consists of liquid sample particles, liquid solvent particles and the carrier gas. This mixed fluid is heated by the evaporator 330, to evaporate only the solvent particles in the mixture. The mixed fluid 85 from the evaporator 330 as consists of the nebulized sample, the evaporated solvent and the carrier gas is further conducted to the cold trap 350 functioning as the cooler. When the mixed fluid 85 passes through the condenser tube 351, only the evaporated solvent thereof is condensed on the inside wall surface of the tube and is discharged as a drain. The fact that when the evaporated solvent is condensed, the nebulized sample moving by acquiring suitable kinetic energy is hardly re-dissolved into the solvent condensed, has been reported in G. W. Dickinson and V. A. Fassel, "Emission Spectric Detection of The Elements At The Nanometer Per Milliliter Level Using Induction, Coupled Plasma Excitation," Analytical Chemistry, 41 (1969) 1021–1024. The mixed fluid 90 from which the solvent and a part of the carrier gas have been removed is guided to the ion source 202 of the MS 20. In the ion source 202, the sample particles are endowed with charges, are decomposed into respective molecules and are ionized. It has been confirmed by the inventors' experiments that the ionization of the sample particles does not always require the evaporation but that it is satisfactorily achieved by the nebulization. The ionized sample is fed to the analyzer tube 204, and is collected by the collector 208. Signals from the collector 208 are amplified by the amplifier 210, with the result that a mass spectrum 2000 is obtained.

The ion source 202 of the MS 20 in the present embodiment is one of the electron impact ionization type. As the ion source 202, one of the chemical ionization type can also be used. In this case, a reagent gas is used instead of the inert gas which is supplied to the nebulizer 310. With the ion source of this chemical ionization type, the ionization can be performed under a pressure higher than that with the ion source of the other type. Therefore, the pressure of the mixed fluid 90 from the interface 30 may be comparatively high. The gas of butane, for example, is used as the reagent gas.

Figure 2:
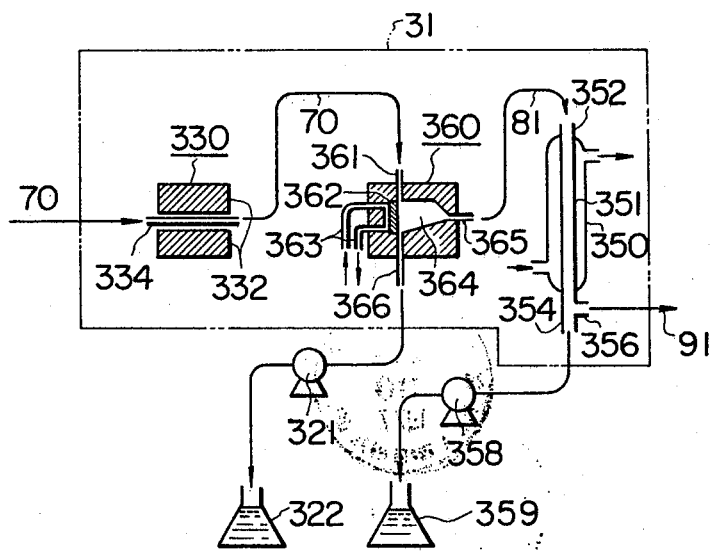
FIG. 2 shows another interface according to this invention, the interface being interposed between a liquid chromatograph and a mass spectrometer.

FIG. 2 shows another embodiment of this invention. An interface 31 consists of an evaporator 330, a nebulizer 360 and a cold trap 350, and is interposed between the LC and MS likewise to the interface 30 shown in FIG. 1. In FIG. 2, the same reference numerals as in FIG. 1 indicate the same or corresponding parts. In this embodiment, the nebulizer 360 intervening between the evaporator 330 and the cold trap 350 is of another type. The nebulizer 360 differs from the nebulizer 310 in FIG. 1 only in that the carrier gas inlet 317 is not provided, and the other structure is the same as in FIG. 1. The effluent 70 from the LC as has received energy, i.e., heat from the evaporator 330 is introduced into the nebulizer 360 through an effluent inlet 361, and it is nebulized on the surface of an ultrasonic transducer 362. At this time, only the solvent in the heated effluent 70 is evaporated. The sample nebulized by the pressure of the evaporated solvent becomes a mixed fluid 81, and is conducted to the cold trap 350. A mixed fluid 91 which has the evaporated solvent removed by the function of the cold trap 350 is fed to the ion source of the MS. The interface 31 as described above is applied to a combined liquid chromatography - mass spectrometry system which includes the MS having the electron impact ionization type ion source.

Figure 3:
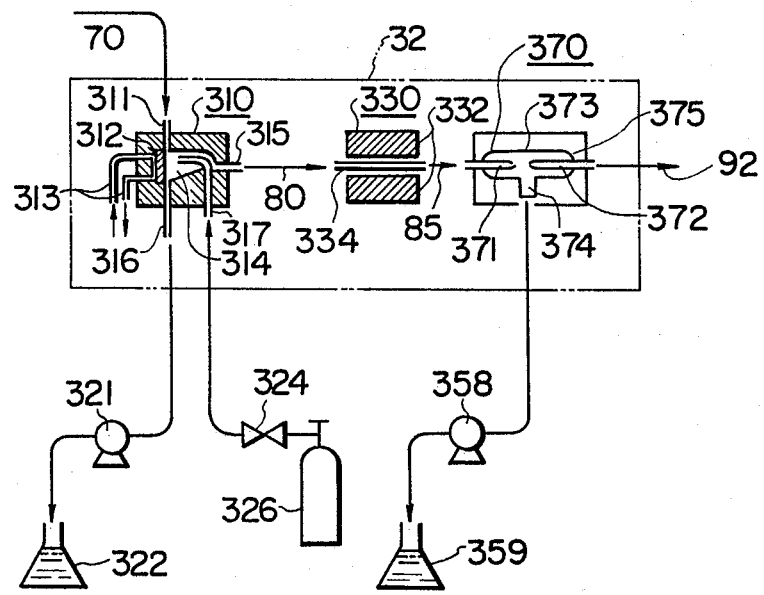
FIG. 3 shows still another interface according to this invention, the interface being similarly interposed between a liquid chromatograph and a mass spectrometer.

FIG. 3 shows still another embodiment. An interface 32, which is also interposed between the LC and the MS, is constructed of a nebulizer 310, an evaporator 330 and a jet separator 370. Also in this figure, the same reference numerals as in FIG. 1 indicate the same or corresponding constituents. The jet separator 370 is made up of first and second nozzles 371 and 372 opposing to each other, a separator tube 373, an evacuation port 374 and a separator oven 375. The first nozzle 371 is connected to the inner tube 334 of the evaporator 330, while the second nozzle 372 is connected to the ion source (not shown) of the MS. The evacuation port 374 of the separator tube 373 is connected to the evacuation pump 358, and the interior of the tube 373 is held at a vacuum.

The mixed fluid 85 from the evaporator 330 as consists of the carrier gas, the evaporated solvent and the nebulized sample is divided into a gaseous fluid including the carrier gas as well as the evaporated solvent and nebulized sample particles. The jet separator 370 separates the gas and the particles by exploiting the difference of their masses. The mixed fluid 85 is introduced into the first nozzle of the jet separator 370, and is injected as a jet into the vacuum space inside the separator tube. The gaseous fluid composed of the carrier gas and the evaporated solvent is diffused, and is discharged to the exterior by the function of the evacuation pump 358. In contrast, the particles of the nebulized sample exhibiting a great mass as compared with the masses of the carrier gas and the evaporated solvent proceed towards the opposing second nozzle 372 and are guided thereinto, and they are further conducted to the ion source of the MS. Such interface 32 can lower the pressure of the mixed fluid down to a considerable extent in the jet separator 370, and is suitable for the MS of the electron impact ionization type. It is also possible to mount the jet separator 370 as described above on the other lower outlet 356 of the cold trap 350 in the interface 30 or 31 illustrated in FIG. 1 or FIG. 2. In this case, the gaseous components remaining in the fluid 90 of the nebulized sample from the cold trap 350 can be further removed.

Figure 4:
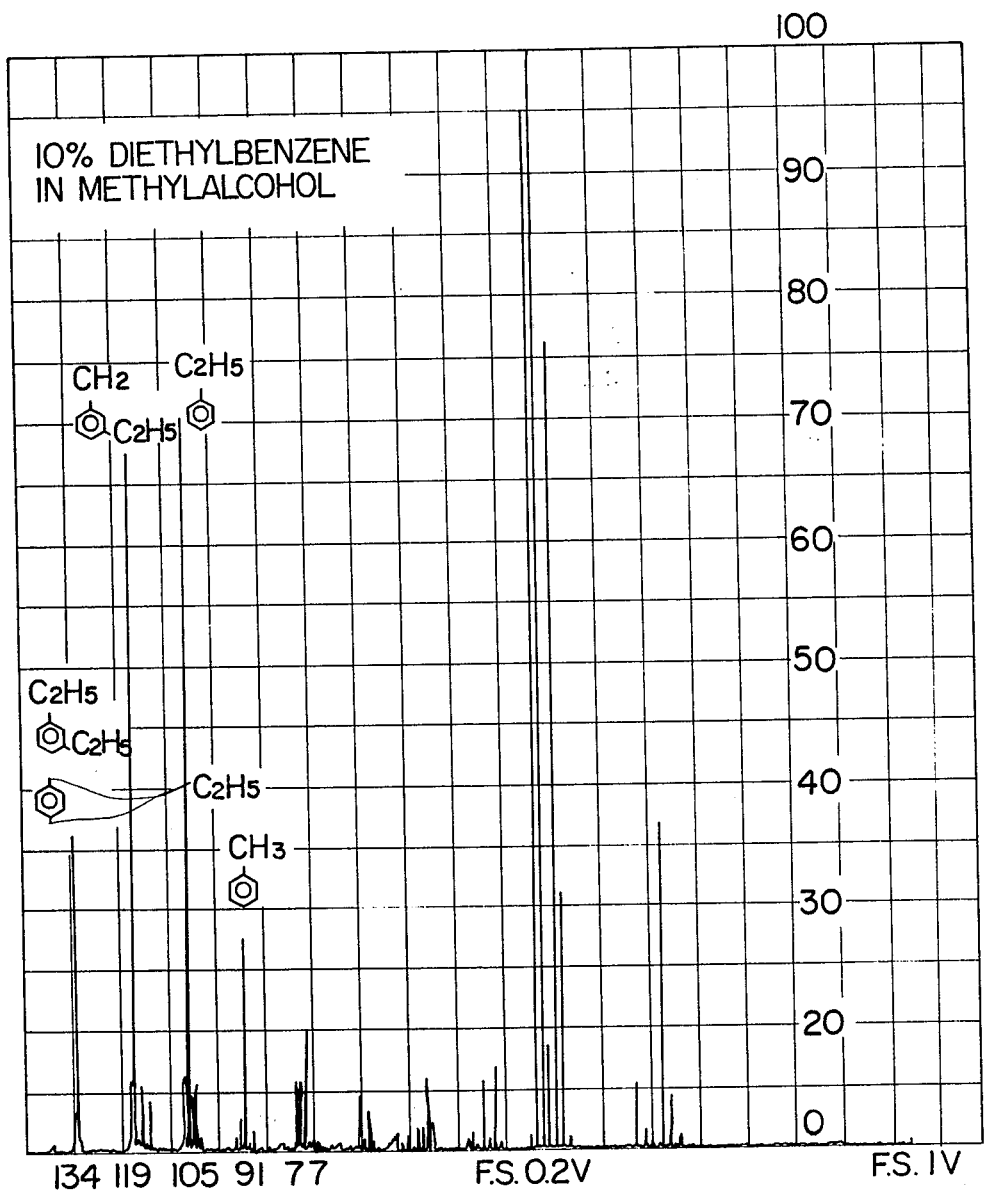
FIG. 4 shows the mass spectrum of diethylbenzene as obtained by the use of the combined liquid chromatography mass spectrometry system of this invention.

FIG. 4 shows a diagram with a part of the mass spectrum of 10%-diethylbenzene enlarged, the mass spectrum having been obtained with the combined liquid chromatography — mass spectrometry system to which the interface constructed according to this invention is applied. As apparent from the diagram, a perfect mass spectrum of diethylbenzene could be obtained even by introducing the nebulized sample into the mass spectrometer.

What we claim is:

1. An interface for use in a combined liquid chromatography — mass spectrometry system which extracts a sample component out of the effluent including the sample component and a solvent component from a liquid chromatograph and supplies the extracted sample component for a mass spectrometer, characterized in that the interface comprises first means for nebulizing the effluent from the liquid chromatograph and heating it in a manner that only the solvent component is evaporated, and second means for separating said nebulized effluent into the nebulized sample component and the evaporated solvent component to extract and supply only the nebulized sample component for the mass spectrometer.

2. An interface as claimed in claim 1, characterized in that said first means comprises nebulizing means connected to the liquid chromatograph and for nebulizing the effluent therefrom, and heating means connected between said nebulizing means and said second means and for heating the nebulized effluent from said nebulizing means in the manner that only the solvent component is evaporated.

3. An interface as claimed in claim 1, characterized in that said first means comprises a heating means connected to the liquid chromatograph for giving energy to the effluent therefrom, and a nebulizing means connected between said heating means and said second means for nebulizing the energized effluent from said heating means, said energization of the effluent being to the extent to which the evaporation of only the solvent component occurs during the succeeding nebulization.

4. An interface as claimed in claim 1, characterized in that said second means has a cooling means which separates the evaporated solvent component from the nebulized effluent from said first means by condensing the evaporated solvent component.

5. An interface as claimed in claim 1, characterized in that said second means has a jet separator means which separates the nebulized effluent from said first means into nebulized sample and the evaporated solvent component according to the difference between the molecular weight of the evaporated solvent and the particle weight of the nebulized sample.

6. An interface as claimed in claim 2, characterized in that said first means further comprises a carrier gas supplying means for supplying said nebulizing means with a carrier gas in order to carry the nebulized effluent from said nebulizing means to said second means.

7. An interface as claimed in claim 4, characterized in that said second means further comprises a jet separator means provided between said cooling means and the mass spectrometer, which further removes the remaining evaporated solvent included within the nebulized sample from said cooling means according to the difference between the molecular weight of the evaporated solvent and the particle weight of the nebulized sample.

* * * * *